United States Patent [19]

Sachs et al.

[11] 4,427,483

[45] Jan. 24, 1984

[54] MICROELECTRODE FABRICTING APPARATUS

[75] Inventors: Frederick Sachs, Buffalo; Richard G. McGarrigle, Eggertsville, both of N.Y.

[73] Assignee: The Research Foundation of State University of New York, Albany, N.Y.

[21] Appl. No.: 371,550

[22] Filed: Apr. 26, 1982

Related U.S. Application Data

[63] Continuation-in-part of Ser. No. 326,386, Dec. 1, 1981, abandoned.

[51] Int. Cl.³ .......................... C23F 1/02; C23F 1/00; C23F 3/00; B44C 1/22
[52] U.S. Cl. .................................... 156/345; 156/664
[58] Field of Search ............ 204/129.1, 129.2, 129.25, 204/129.5, 129.55, 129.6, 195 G, 219, 220, 221, 224 R, 225, 224 M, 250; 427/125, 258, 273; 156/625, 627, 628, 654, 345, 664, 656; 75/100, 75/118 R

[56] References Cited

U.S. PATENT DOCUMENTS

| | | | |
|---|---|---|---|
| 3,052,618 | 9/1962 | Deprez et al. | 204/225 |
| 3,205,155 | 9/1965 | Van Natter | 204/130 |
| 3,388,047 | 6/1968 | Higgins | 204/15 |
| 3,707,467 | 12/1972 | Chilton et al. | 204/250 |
| 4,082,639 | 4/1978 | Ralston et al. | 204/219 |

FOREIGN PATENT DOCUMENTS 245514  10/1969  U.S.S.R. .................... 204/129.55

OTHER PUBLICATIONS

Sachs et al., "An Almost Completely Shielded Microelectrode", Journal of Neuroscience Methods, 3(1980), pp. 151–157.

*Primary Examiner*—Howard S. Williams
*Assistant Examiner*—T. Williams
*Attorney, Agent, or Firm*—Michael L. Dunn; Howard M. Ellis

[57] ABSTRACT

Apparatus for controlled removal of silver from the tip of a silver coated microelectrode including a mercury bath aligned with the microelectrode; a motor driven micromanipulator for moving the microelectrode into contact with the mercury; and circuits to deenergize and control the angular momentum of the micromanipulator motor whereby the depth of penetration of the electrode into the mercury can be accurately controlled.

12 Claims, 8 Drawing Figures

MICROELECTRODE FABRICTING APPARATUS

This invention is a continuation-in-part of application Ser. No. 326,386, filed on Dec. 1, 1981, now abandoned.

BACKGROUND OF THE INVENTION

The present invention relates to an apparatus for fabricating microelectrodes.

Microelectrodes are widely used in electrophysiology for recording potentials, passing currents or for iontophoresis. These microelectrodes are usually fabricated of glass pipettes having a central opening therethrough, the tip of which is adapted to be placed in a tissue bath or the like for the above-mentioned sensing or probing purposes. These electrodes are filled with a conducting electrolyte such as KCl or NaCl solution. However, at audio frequencies, the electrodes capacitance to the tissue bath and to adjacent electrodes can cause interference and reduced fidelity. In an attempt to overcome these problems, various techniques of or forms of electrical shielding have been proposed.

For example, the provision of a driven shield over a voltage recording electrode has the desirable effect of reducing the effective capacitance of the electrode to thereby permit higher bandwidth recordings. During iontophoresis and recording employing a multiple barrel pipette or electrode, the response time of the recording pipette is reduced due to the pipettes capacitance to the neighboring iontophoretic barrels as well as its capacitance to the tissue bath. In addition, voltage fluctuations generated by the passage of current through the iontophoretic barrels can cause electrical noise in the recording barrel. Electrodes are known wherein a graphite aerosol has been used to shield the recording microelectrode to within 1 mm of the tip thereof. For a typical microelectrode-to-bath capacity of $1_pF/mm$, however, this 1 mm tip exposure produces too much capacitance for more demanding application such as microelectrode voltage clamping or high fidelity impedance measuring.

One of the major drawbacks in the employment of microelectrode voltage clamps is the unavoidable capacitance between the current and the voltage electrode which combines with the resistance thereof to form an RC circuit to thereby introduce a time lag or constant that significantly slows down the response or recording process. Electronic compensation has been proposed, in an attempt to overcome this problem, by partially cancelling the interelectrode capacities. However, the success of such electrode compensation techniques is subject to the variabilities in the electrodes themselves, foremost among which is the resistance of the current electrode. Further, such compensation techniques introduce excessive noise in that amplifier noise fed through the compensation capacity is added to the membrane potential. It is, therefore, extremely crucial to reduce or minimize the capacitance between the current and voltage electrodes.

Heretofore, the common method of shielding microelectrodes has been to simply apply silver paint to the same with the aid of a suitably powered microscope. However, the grain size of silver paint is large and the painting process is tedious, especially if it is desired to shield close to the tip of the microelectrode.

SUMMARY OF THE INVENTION

The foregoing problems, as well as other problems not specifically mentioned, are overcome according to the teachings of the present disclosure, which provides a microelectrode and process for shielding and insulating the same whereby a conductive layer of shielding material is coated exteriorly thereof to within substantially 20 micrometers or less of the tip thereof and is sandwiched between an insulating layer extending below the conductive layer and adhering to the electrode without clogging the central throughopening at the tip thereof.

In the context of the present disclosure in order to optimally shield the microelectrodes the shield:
1. must be highly conductive;
2. must not interfere with penetration;
3. must be insulated from the surrounding aqueous media; and
4. should lend itself to relatively simple and repeatable construction.

That these requirements are adequately satisfied according to the teachings of the present disclosure will become apparent hereinbelow.

Essentially the method according to the disclosure includes the steps of; coating the exterior surface of a microelectrode having a central throughopening by vacuum evaporation techniques to provide a thin layer of conductive material thereabout; removing a controlled layer of conductive material from a circumferential tip area of the microelectrode leaving a tip region thereof exposed; and inserting said microelectrode into an insulating material in liquid form whereby as the insulating material solidifies about the microelectrode the layer of conductive material and a portion of the tip region is completely covered thereby leaving the remainder of the tip region and the central throughopening of the microelectrode fully exposed.

The evaporative deposition provides a very thin uniform layer of highly conductive material without clogging the open tip of the microelectrode, whereas the liquid insulating material adequately provides a complete dielectric covering for the conductive material without, similarly, clogging the tip opening and, yet, leaving a very small thin-walled electrode tip for adequate penetration into the tissue bath, incidental to the routine use thereof.

The resulting shielded microelectrode product according to the present disclosure includes a microelectrode body; a central throughopening passing from the shank end of the body to the operative tip end thereof; a coating of conductive material adhering in surrounding relation to the exterior of the body short of the tip thereof to thereby leave an exposed exterior tip portion of no greater than 20 micrometers.

In this manner the capacitance of the exposed tip region is reduced to a minimum and, consequently, the above-noted capacitance-related problems are significantly reduced, if not entirely eliminated.

The apparatus according to the present invention provides means for automatically and accurately removing the conductive material from the tip region of the microelectrode, in a precisely controlled fashion, prior to the application of the insulating material.

Essentially, such means for conductive material removal includes a motorized micromanipulator; a microelectrode coated with a conductive material carried by the micromanipulator for bidirectional movement therewith; a mercury bath located adjacent the coated tip of the microelectrode; circuit means for causing the micromanipulator to move the microelectrode tip into contact with the mercury and sensing means responsive to such contact for actuating said circuit means whereby the microelectrode tip penetrates the mercury to a predetermined depth for precise conductive material removal therefrom.

BRIEF DESCRIPTION OF THE DRAWINGS

For a fuller understanding of the present invention and its characterizing features reference should now be made to the following detailed description thereof taken in conjunction with the accompanying drawings; wherein.

DETAILED DESCRIPTION OF THE PREFERRED EMBODIMENT

Figure 1:
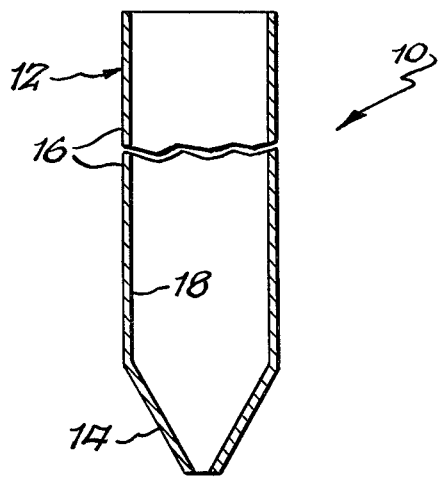
FIG. 1 is a schematic cross-sectional view of the microelectrode, greatly enlarged for ease in illustration.

In practising the method of the present disclosure a standard microelectrode is employed, as depicted generally at 10 in FIG. 1. Electrode 10 is of needle-like construction having a shank end 12, a tapered operative tip end 14, an exterior surface 16 and a hollow interior through passage or opening 18, extending from the shank end to the tip end. Microelectrode 10 may be suitably fabricated of glass.

Figure 2:
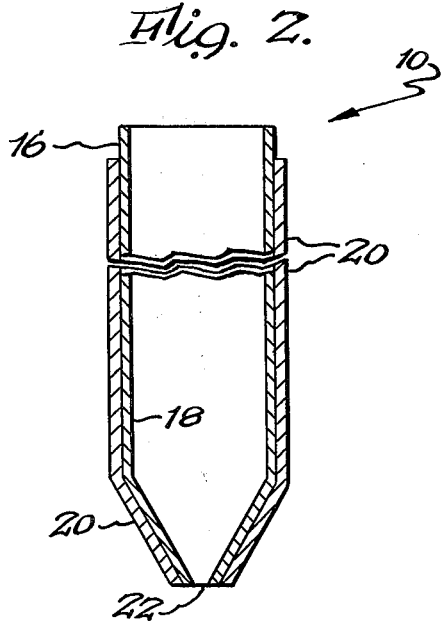
FIG. 2 is a view similar to FIG. 1 but depicting the microelectrode after the same has been coated with the thin layer of conductive or shielding material.

A suitable highly conductive material, such as silver or gold from the noble metal group is completely deposited on the microelectrode 10 to form a thin uniform layer of conductive metal 20, as depicted in FIG. 2, without clogging the tip opening 22 of the microelectrode. To accomplish this coating process any well known vacuum evaporation techniques may be employed. For example, the microelectrode may be placed tip up on a teflon disk drilled to accommodate about 50 electrodes. The disk and electrodes, after being rinsed in acetone may then be attached to the shaft of a sample rotator in a vacuum evaporator of the type used for shadowing in electron microscopy. Next, a few hundred milligrams of silver wire may be placed in an evaporation basket at a distance of approximately 10 cm from the electrodes and the evaporation is run to completion (about 4 minutes). The evaporation leaves the electrodes completely coated with silver except for about 3 to 4 cm at the shank end 16.

The next step in the process is to remove a controlled amount of the conductive material (silver in this example) from the tip of the microelectrode. To this end, the electrode may be mounted in a micromanipulator observed under a microscope and the tip thereof may be touched to a small ball of mercury resting in a petri dish. The silver and mercury form an amalgam which immediately dissolves the silver from the tip 14. The negative meniscus of the mercury prevents the same from creeping up the electrode such that by careful manipulation, the silver may be removed in a controlled fashion for distances of only a few microns from the electrode tip. In fact, as shown at d in FIG. 3, it is possible to reduce the tip exposure to a depth of 20 micrometers or less. This step is simple, reliable, and, most importantly, does not clog the tip of the electrode. However, as will become apparent hereinbelow, the present invention provides an apparatus for automatically and repeatedly removing a controlled amount of silver without reliance upon the skill and dexterity of an operator as would be the case with the aforementioned manual technique.

Figure 4:
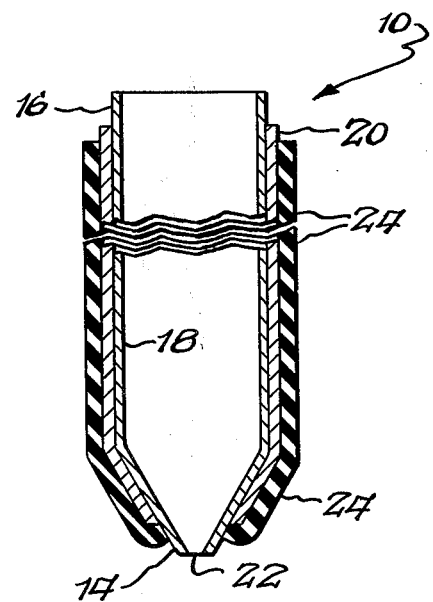
FIG. 4 is a view similar to FIG. 3 but depicting the final microelectrode product after the insulation has been applied thereto.

The final step of the process is that of insulating the shielded microelectrode. It has been found that dipping the electrode, tip first, in a bath or reservoir of liquid insulating material of proper viscosity and surface tension results in satisfactory insulating coatings which leave the electrode tip clear and unclogged, as depicted at 24 in FIG. 4. More specifically, the electrode is dipped into a vial or the like of liquid insulating material and held tip down for a few seconds and removed to allow the insulating material to harden. Surface tension withdraws excess insulating material upwardly along the tapered tip 14 of the electrode to thereby leave the tip clear and unclogged and to provide a hardened layer of material that completely surrounds and insulates the conductive layer or shield 20. Examples of insulating material evidencing satisfactory results and having desirable properties of viscosity and surface tension in their liquid state are "Crown Sticky Wax" manufactured by S. S. White of Philadelphia, Pa. and "Pyseal" C-228 available from Fisher Scientific. It has been found that the "Crown Sticky Wax" should be conditioned after being melted by boiling the same for a few hours until the liquid turns from its original rust color to a dull green. With the "Pyseal" wax, no such conditioning has been required. It should be understood, however that any other suitable insulating material or thermosetting waxes exhibiting similar viscosity and surface tension properties are contemplated.

It should, thus, be apparent that the process of the present disclosure accomplishes its objectives of simply, yet accurately, shielding the microelectrode tip to a depth of 20 micrometers or less, and insulating the same to a resistance of at least $10^{10}$ ohms with stray capacitance thereat reduced to about 1 $_pF$/mm of exposed tip. Thus, for 20 micrometers of exposed tip, stray capacitance would be only about 20 fF.

It should be understood that the step of removing or dissolving the conductive material from the microelectrode can be accomplished by automatic means for reproducibility and speed. To this end, a motorized micromanipulator may carry the coated microelectrodes above a suitable support, for the mercury droplet, and drive the same at precisely controlled speed to the desired contact therewith for precise conductive material removal. A feedback circuit may be provided to sense contact of the microelectrode with the mercury and a suitable timing circuit may be provided to ensure sufficient time for amalgam formation and conductive material removal. An electronic controller may be provided for driving the micromanipulator and for variably controlling the timing functions and the speed of the micromanipulator motor.

Figure 3:
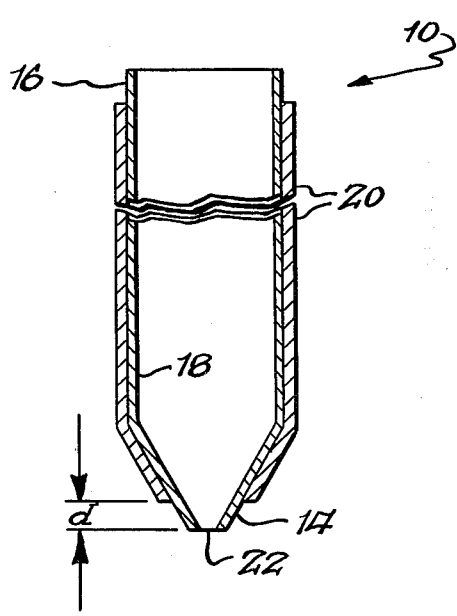
FIG. 3 is a view similar to FIG. 2 but depicting the microelectrode after removal of the conductive layer from a tip region thereof.

More specifically, in accordance with the present invention, an apparatus is provided which (under the control of suitable electronics) functions to automatically lower the coated microelectrode into mercury whereby the conductive coating of silver or the like may be consistently and repeatedly removed to the desired depth from the tip region thereof, as depicted at d in FIG. 3.

Figure 5:
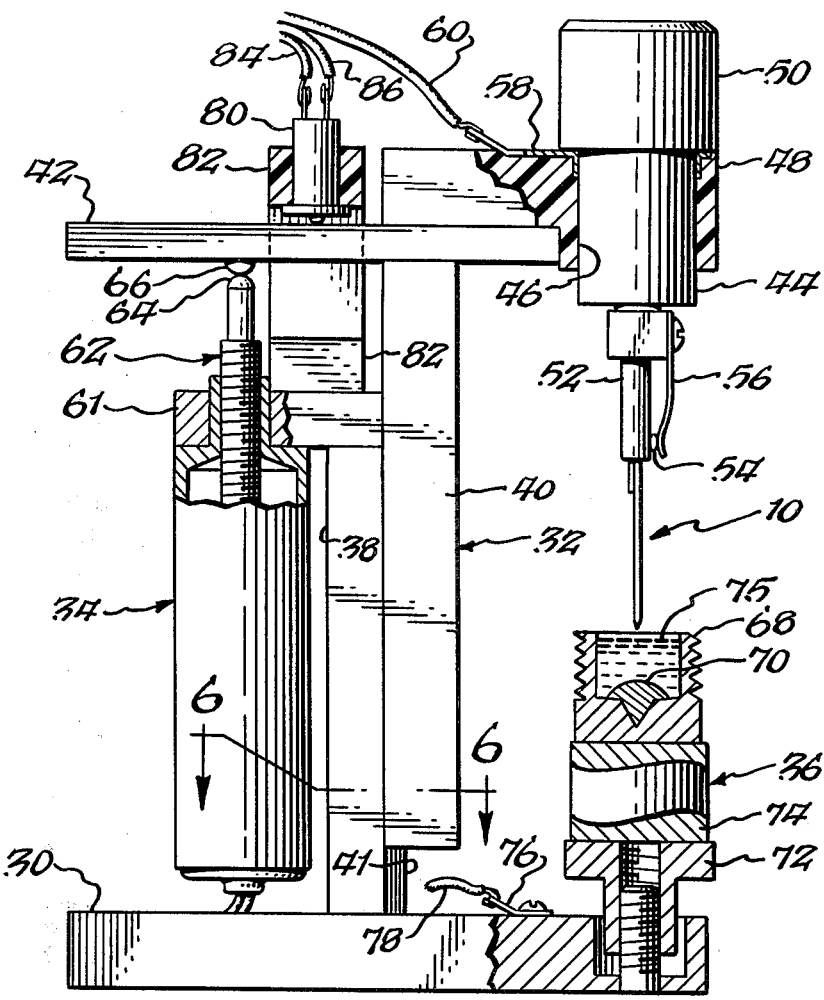
FIG. 5 is a side elevational view, partially in section, of the conductive material removal apparatus of the present invention.
Figure 6:
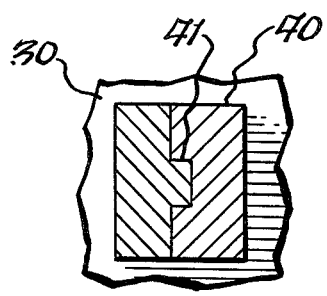
FIG. 6 is a fragmentary sectional view taken substantially along line 6—6 of FIG. 5.

Referring in detail to FIGS. 5 and 6, such apparatus may include a base 30, fabricated of brass or the like, upon which is mounted a substantially vertical slide assembly 32, a motorized micrometer 34 and a suitable reservoir or mercury bath container assembly 36.

Slide assembly 32 may be of conventional construction and is depicted as comprising a stationary upright or column 38; a vertically moving slide element 40, suitably keyed at 41 for reciprocable motion with respect to upright 38; and a horizontally disposed plate or platform 42 affixed to or suitably supported by the upper end of slide element 40.

An electrode holder 44 of generally cylindrical construction is fitted within a vertically disposed throughbore 46 of a support member 48 and is provided with an enlarged diameter head 50 which may freely and removably rest upon support member 48. In turn, support member 48 may be suitably affixed to a platform 42 for movement therewith. Holder 44 is provided at its lower end with means to detachably secure the coated microelectrode 10 thereto. To this end, the lower end of holder 44 may be provided with a chuck-like member 52 to receive the shank end of microelectrode 10, which may be held in place by a slide pin 54 biased by a spring clip 56. Support member 48 is fabricated of a suitable dielectric material such as lucite and has interposed between head 50 and the upper surface thereof a contact or terminal plate 58 to which an electrical lead 60 is affixed, for a purpose to become apparent hereinbelow. Holder 44, head 50 and chuck 52 are made of a metallic material.

Slide 40, platform 42, support member 48, electrode holder 44 and microelectrode 10 are driven by the motorized micrometer 34, the housing of which may be suitably supported by upright 38 by means of a plate 61 at the upper end thereof. The output, motor driven, threaded shaft 62 of micrometer 34 is provided at its upper end with a partially spherical head 64 which is in abutting engagement with a captive ball bearing 66, rotatably contained within the undersurface of platform 42, whereby helical movement of shaft 62 causes only reciprocation of platform 42 and microelectrode 10 supported thereby. The bearing 66 and head 64 function to reduce wear between shaft 62 and platform 42. Inasmuch as the motorized micrometer or micromanipulator 34 is of conventional construction and commercially available, no further specific description thereof is deemed necessary.

Mercury bath container assembly 36 may include a reservoir 68 for containing a droplet of mercury 70, an adjustable support 72 fixed to base 30 and means to removably attach reservoir 68 to support 72. Such means may conveniently comprise a cylindrical magnet 74. All components of the bath assembly are fabricated of a conductive material, such as steel, and the base 30 is suitably grounded as by contact terminal 76 and lead wire 78. The mercury 70 may be covered with amyl acetate 75 or other similar liquid to remove organic material which might otherwise prevent complete contact between microelectrode 10 and the mercury.

Completing the apparatus as depicted in FIGS. 5 and 6 is a suitable upper limit switch assembly 80 which is mounted upon a substantially C-shaped support 82; the bottom leg of which being suitably affixed and carried by plate 61. Support 82 is fabricated of a dielectric material such as lucite and straddles platform 42 whereby contact of switch 80 is aligned for abutting engagement therewith to limit the upward travel thereof. Lead wires 84 and 86 extend from switch assembly 80 to provide a signal indicative of the closure thereof in contact with platform 42.

Figure 7:
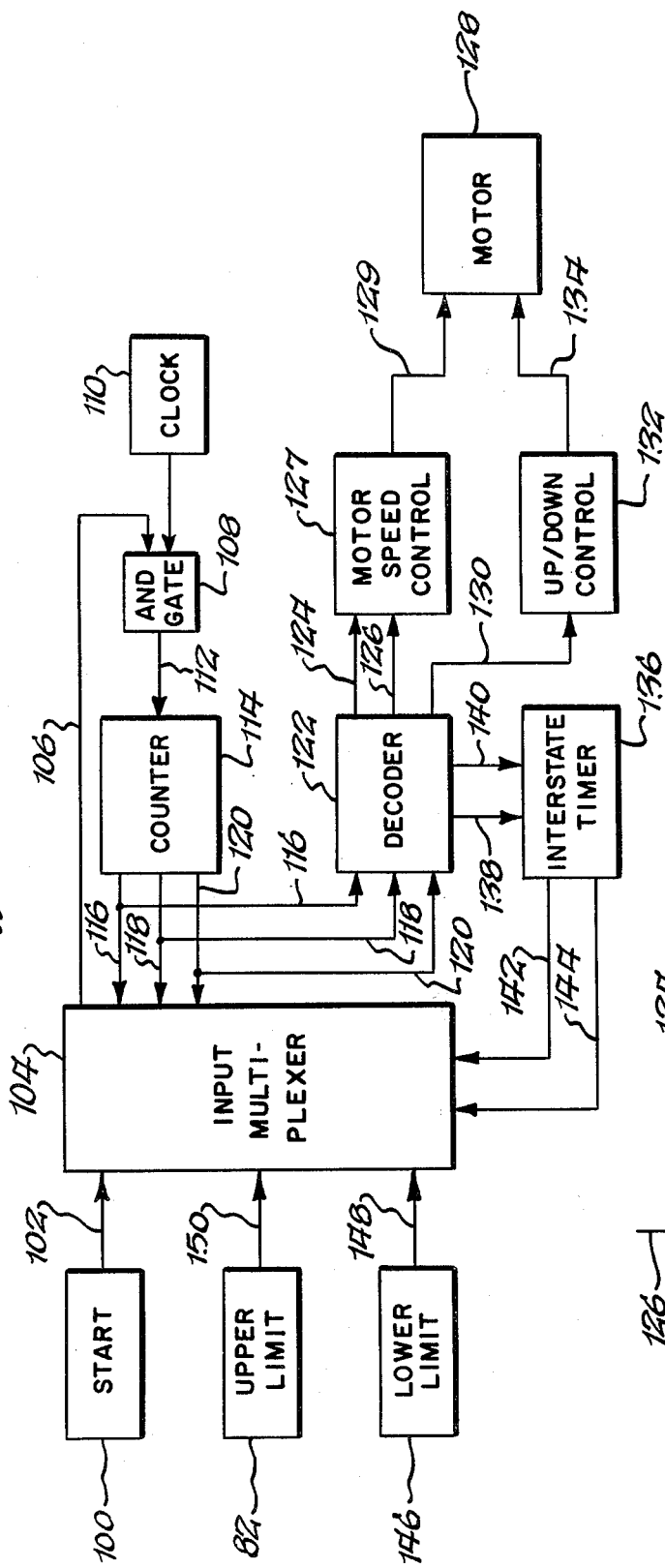
FIG. 7 is a flow diagram, in block form, depicting exemplary electronic components for controlling the apparatus of FIG. 5.
Figure 8:
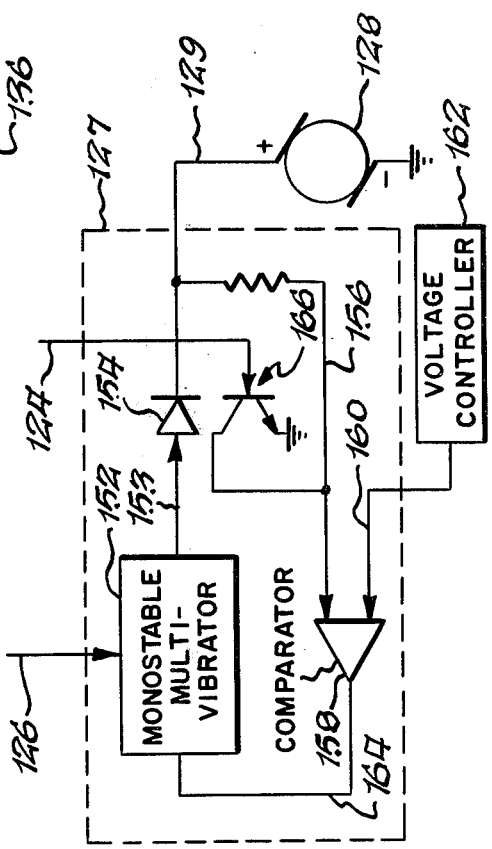
FIG. 8 is a detailed schematic view of the motor speed control of FIG. 7.

Prior to the ensuing description of the exemplary control circuit of FIGS. 7 and 8, it will be instructive to indicate the functional sequence of operations performed thereby in connection with the above-described apparatus of FIGS. 5 and 6.

In the position shown in FIG. 5, the silver coated electrode 10 is located in vertically spaced and aligned relation to the mercury 70. When the motor of assembly 34 is energized the shaft 62, the platform 42 and the microelectrode 10 are simultaneously lowered at a relatively high rate of speed to bring the tip of the microelectrode very close to the mercury droplet 70. At this position, the motor speed is significantly reduced and the microelectrode continues its downward travel until the same makes contact with the mercury whereupon a circuit is closed and a signal is developed through lines 60 and 78 due to the electrical continuity established at electrode-mercury contact. At this contact, the micrometer motor is essentially deenergized and the desired depth of penetration of the electrode into the mercury is accomplished by precisely controlling the angular momentum or inertial response of the motor at deenergization thereof. After a short period of time, sufficient to ensure complete silver removal from the tip region of the microelectrode, the motor is energized in a reverse direction to raise the platform and the electrode at a relatively fast speed to the position shown in FIG. 5 whereat the platform contacts and closes upper limit switch 80. At switch closure, the micrometer motor is stopped and the cycle has been completed.

The foregoing functions are accomplished by the control circuitry depicted in FIGS. 7 and 8 which will now be discussed. However, it is to be understood that the circuit components illustrated are exemplary of one embodiment and should, therefore, not be necessarily interpreted as limiting the scope of the present invention.

It should be appreciated from the foregoing sequence of operations, that five signals are necessary to properly control the silver removal apparatus. Specifically, a start signal to initiate microelectrode lowering at a relatively fast speed; a slow speed signal to terminate fast speed operation at a predetermined time after initiation thereof and to slowly lower the microelectrode until contact with the mercury; a mercury contact signal that initiates microelectrode penetration to a precisely controlled depth; a motor reverse signal to raise the microelectrode after a period of time in the mercury; and an upper limit signal to stop the micrometer motor after the electrode has been lifted to its initial position, ending the cycle.

The start signal, initiated by pressing a contact or the like 100 on a control panel, is fed via line 102 through an input multiplexing 104 and thence via common line 106 to an AND gate 108. When the signal to gate 108 coincides with pulses or signals from a clock 110, an output signal is fed via line 112 to a state counter 114. Counter 114 is advanced to its next state and delivers an appropriate signal or combination of signals via lines 116, 118 and 120 back to multiplexer 104 to block further signals from line 102 and to prepare the multiplexer for the next input signal. The combination of signals in lines 116, 118 and 120 are suitably interpreted by a decoder 122 which triggers, via lines 124 and 126, a motor speed control circuit 127 to start and cause relatively high speed operation of the micrometer motor 128, via line 129. At the same time the signals from the decoder 122 also triggers, via line 130, directional control circuit 132 to cause the motor 128 via line 134 to drive shaft 62 and microelectrode 10 in the downward direction. The duration of downward travel is controlled by one of two timing circuits, within the circuit block depicted as interstate timer 136, in response to a decoder signal on one of lines 138 and 140. The duration of this timing function may be suitably varied by the operator and at the completion thereof an end signal is fed, via one of lines 142 and 144, back through multiplexer 104 and line 106 to gate 108. An output in line 112 from gate 108 advances counter 114 to its next state which, in turn, delivers appropriate combinations of signals via lines 116, 118 and 120 to multiplexer 104 to prepare the same for its next input. Decoder 122, in response to these combination of signals, delivers (via line 124) a trigger signal to motor speed control 127 which initiates slow speed operation of the micrometer motor 128.

Slow speed operation continues until microelectrode 10 contacts the memory 70 and establishes electrical continuity between lines 60 and 78 in the manner of a lower limit switch, as depicted schematically at 146 in FIG. 7. A signal from 146 is fed via line 148 through multiplexer 104 to line 106 and thence to AND gate 108. An output in line 112 from gate 108 advances counter 114 to its next state which delivers appropriate combinations of signals via lines 116, 118 and 120 to multiplexer 104 to set the same for its next input. Decoder 122, in response to these signals delivers a signal via line 126 to trigger stoppage of motor 128 through motor speed control circuit 127. At the same time, decoder 122 delivers a signal via the other of lines 138 and 140 to interstate timer 136 to initiate the second timing function thereof. This time period allows the microelectrode 10 to remain in the mercury 70, at the desired depth, sufficiently long enough to ensure silver removal from the tip region thereof. At the completion of this time period, a signal is fed from timer 136 through the other of lines 142 and 144 through multiplexer 104 and line 106 to AND gate 108. An output in line 112 from gate 108 advances counter 114 to its next state which, in turn, delivers an appropriate combination of signals (via lines 116, 118 and 120) to multiplexer 104 to set the same for its next input.

These combinations of signals are also fed to decoder 122 which, in response thereto, simultaneously triggers (via lines 124, 126 and 130) fast speed travel of the motor in its upward direction. When platform 42 contacts upper limit switch 82, a signal is fed via line 150 through multiplexer 104 and line 106 to AND gate 108. An output in line 112 from gate 108 advances counter 114 to its start state and multiplexer 104 is again set to receive a start command from 100, whereby the above-described sequence of events is ready to be repeated.

Signals are also fed from decoder 122 to motor speed control 127 to stop motor 128.

It should thus be apparent that the circuit components of FIG. 7 function as means to cause the microelectrode 10 to travel downwardly towards the mercury 70 at a relatively fast rate of speed until the same is adjacent thereto; as means to reduce the speed of the microelectrode until contact is made with the mercury; as means to stop the motor such that the angular momentum thereof carries the microelectrode to the desired depth within the mercury; as means to maintain microelectrode penetration for a predetermined period of time; and as means to reverse the direction of the motor to cause upward travel of the microelectrode. Further, at the completion of each of the above sequence of events, appropriate feedback signals are provided to sequentially initiate the next event.

An exemplary speed control circuit is depicted in FIG. 8, including means to precisely control the speed of motor 128 such that, at deenergization thereof, the microelectrode will be permitted to penetrate the mercury to the desired depth for silver removal from the tip region thereof.

Motor 128 may comprise a DC motor that is driven by pulses from a continuously retriggerable monostable multivibrator 152. More specifically, multivibrator 152 (set on or off by signal in line 126) delivers output pulses (suitably amplified) in line 153 to rectifier 154 to cause energization of the motor in a well known manner. The speed of the motor is set by controlling the spacing of output pulses from monostable vibration 152. When there is no pulse in line 129, the motor free runs and develops a back EMF signal in line 156. A comparator 158 compares this back EMF signal with a reference signal in line 160 from a voltage controller 162, which may comprise a manually variable potentiometer or the like. When the back EMF signal falls to the value of the signal in line 160, the comparator 158 delivers a trigger output signal in line 164 to retrigger multivibrator 152 thereby causing the same to feed another pulse to motor 128 to increase the speed thereof. Thus, the value of the signal in line 160 controls the speed of motor 128, increasing the same when high and decreasing the same when low. It is significant to note that the setting of voltage controller 162 to control the speed of the motor will also effect the inertia or angular momentum thereof until the same comes to a stop. Thus, in the absence of an output signal from multivibrator 152 in line 153, the time for motor stoppage will depend upon the speed thereof prior to deenergization which, in turn, is a function of the setting of controller 162; and since depth of penetration of the microelectrode into the mercury is a function of the angular momentum of the motor, then such depth can be precisely controlled by the setting of controller 162.

Fast speed operation of motor 128 is accomplished by grounding the back EMF signal in line 156 in response to the decoder signal in line 124. More specifically, the signal in line 124 causes a transistor 166 to conduct, thereby essentially reducing to zero the signal in line 156 which, in turn, permits a signal in line 164 to continuously retrigger multivibrator 152.

It should be understood that slow speed operation of motor 128 and microelectrode 10 is necessary such that, when the motor is deenergized, the angular momentum thereof is sufficiently slow to achieve the desired depth of microelectrode penetration in the mercury, about 20 micrometers or less. At high speed operation the electrode would penetrate too deep into the mercury. Yet, high speed operation is desirable to efficiently bring the tip of the microelectrode close to the mercury and, thereby, relieve an operator from the burden of waiting inordinately long periods of time for the cycle of silver removal to run to completion and for the platform to return to its upper position.

Although a preferred embodiment of the present invention has been disclosed and described, changes will obviously occur to those skilled in the art without departing from the spirit thereof. It is, therefore, intended that the present invention is to be limited only by the scope of the appended claims.

What is claimed is:

1. A microelectrode fabricating apparatus for automatic and controlled removal of conductive material from the tip of a microelectrode; comprising
    a power driven micromanipulator;
    a microelectrode coated with a conductive material and supported by said micromanipulator for movement therewith;
    a mercury bath in alignment with the coated tip of said microelectrode;
    control means for actuating said micromanipulator to move said microelectrode tip into contact with said mercury; and
    sensing means responsive to said contact with said mercury for actuating said control means whereby said microelectrode tip penetrates said mercury to a predetermined depth for precise conductive material removal therefrom.

2. The apparatus according to claim 1, wherein:
    said micromanipulator includes an output shaft and a motor for driving said output shaft; and
    said control means includes a control circuit to deenergize said motor at said contact, whereby the angular momentum of said motor causes said microelectrode to penetrate said mercury to said predetermined depth.

3. The apparatus according to any one of claims 1 or , wherein:
    said predetermined depth is no greater than substantially 20 micrometers.

4. The apparatus according to claim 3, wherein:
    said control means includes circuits actuable to permit relatively rapid advance of said microelectrode toward said mercury bath until said microelectrode is closely adjacent thereto and to reduce the rate of advance thereof until said contact.

5. The apparatus according to claim 4, wherein:
    said last mentioned circuits include a first timing circuit actuable to control the duration of said relatively rapid advance; and
    a second timing circuit responsive to said contact for maintaining said microelectrode in contact with said mercury for a time sufficient for the removal of said conductive material from the tip thereof to said predetermined depth.

6. The apparatus according to claim 2, wherein:
    said motor is a DC motor driven by a retriggerable monostable multivibrator; and there is further provided
    a comparator responsive to the back EMF signal of said motor and to a predetermined signal for developing an output signal to trigger said multivibrator when said back EMF signal falls to the value of said predetermined signal whereby when said multivibrator is disabled the angular momentum of said motor is a function of the value of said predetermined signal prior to said disablement; and
    said control circuit is actuable to disable said multivibrator in response to said microelectrode contact with said mercury.

7. The apparatus according to claim 6, wherein:
    said control means includes circuits actuable to permit relatively rapid advance of said microelectrode toward said mercury bath until said microelectrode is closely adjacent thereto and to reduce the rate of advance thereof until said contact;
    said circuits include a timing circuit to control the duration of said rapid advance; and
    said control circuit is responsive to said timing circuit to maintain said back EMF signal below the value of said predetermined signal whereby said multivibrator is continuously retriggered.

8. The apparatus according to claim 1, wherein:
    said control means includes a timing circuit actuable in response to said contact to maintain said microelectrode at said predetermined depth for a period of time sufficient for conductive material removal therefrom; and
    means for moving said microelectrode out of contact with said mercury after said period of time.

9. A microelectrode fabricating apparatus for automatic and controlled removal of conductive material from the tip of a microelectrode; comprising:
    a micromanipulator having an output shaft and a motor for driving said output shaft;
    a microelectrode holder supported for movement with said output shaft;
    reservoir means adapted to contain a mercury bath in alignment with said holder;
    motor speed control means for moving said output shaft towards said reservoir at a relatively fast rate until said holder is a predetermined distance away from said reservoir and for substantially reducing the rate of movement thereof thereafter.

10. The apparatus according to claim 9, wherein said motor speed control means includes:
    a retriggerable monostable multivibrator for delivering pulses to drive said motor;
    a comparator responsive to the back EMF signal generated by said motor between said pulses and to a predetermined signal for developing an output signal to trigger said multivibrator when said back EMF signal falls below the value of said predetermined signal whereby said reduced rate of movement is a function of said predetermined signal; and there is further provided
    means for maintaining said back EMF signal below said predetermined signal whereby said multivibrator is continuously retriggered to maintain said fast rate.

11. The apparatus according to claim 10, further comprising:
    means for disabling said multivibrator to deenergize said motor whereby the angular momentum thereof is a function of said predetermined signal prior to deenergization of said motor.

12. The apparatus according to claim 11, further comprising:
    a coated microelectrode carried by said holder;
    mercury contained within said reservoir; and
    said last mentioned means being actuable upon contact between said microelectrode and said mercury whereby the depth of penetration of said mercury is controlled by the angular momentum of said motor and the magnitude of said predetermined signal.

* * * * *